US00PP20828P2

(12) United States Plant Patent
Giesen

(10) Patent No.: US PP20,828 P2
(45) Date of Patent: Mar. 16, 2010

(54) *LAVANDULA* PLANT NAMED 'JIN COBULE'

(50) Latin Name: *Lavandula stoechas*
Varietal Denomination: Jin Cobule

(75) Inventor: Eric Giesen, Andijk (NL)

(73) Assignee: Goldsmith Seeds Europe B. V., Andijk (NL)

( * ) Notice: Subject to any disclaimer, the term of this patent is extended or adjusted under 35 U.S.C. 154(b) by 0 days.

(21) Appl. No.: 12/316,752

(22) Filed: Dec. 16, 2008

(51) Int. Cl.
*A01H 5/00* (2006.01)

(52) U.S. Cl. ..... Plt./445

(58) Field of Classification Search ..... Plt./445, Plt./226

See application file for complete search history.

*Primary Examiner*—June Hwu
(74) *Attorney, Agent, or Firm*—S. Matthew Edwards

(57) ABSTRACT

A new *Lavandula* plant named 'Jin Cobule' particularly distinguished by large, dark blue flower heads with lavender 'wings' well above the foliage, gray-green, fir-needle like leaves, compact, well-branched spreading to mounding plant habit.

1 Drawing Sheet

Latin name of the genus and species of the plant claimed: *Lavandula stoechas*.

Varietal denomination: 'Jin Cobule'.

BACKGROUND OF THE NEW PLANT

The present invention comprises a new and distinct cultivar of *Lavandula,* botanically known as *Lavandula stoechas* and hereinafter referred to by the cultivar name 'Jin Cobule.'

'Jin Cobule' is a product of a planned breeding program. The new cultivar originated from a hybridization made in May 2003 in Andijk, Netherlands.

The female parent was an unpatented, proprietary *Lavandula* plant designated 'LA04-1-1,' having purple flower color. 'LA04-1-1' has a less deep green foliage color and less compact habit than 'Jin Cobule.'

The male parent of 'Jin Cobule' was an unpatented, proprietary *Lavandula* plant designated 'LA03-2-1,' having lavender flower color. 'LA03-2-1' has a less deep foliage color and taller plant size than 'Jin Cobule.'

The resulting seeds were sown in January 2005. 'Jin Cobule' was selected as one flowering plant within the progeny of the stated cross in August 2005 in a controlled environment in Andijk, Netherlands.

The first act of asexual reproduction of 'Jin Cobule' was accomplished when vegetative cuttings were taken from the initial selection in the fall of 2005 in a controlled environment in Andijk, Netherlands.

Horticultural examination of plants grown from cuttings of the plant initiated in the spring of 2006 in Andijk, Netherlands, and in Hillscheid, Germany, and continuing thereafter, has demonstrated that the combination of characteristics as herein disclosed for 'Jin Cobule' are firmly fixed and are retained through successive generations of asexual reproduction.

'Jin Cobule' has not been observed under all possible environmental conditions. The phenotype may vary significantly with variations in environment such as temperature, light intensity and day length.

Plant Breeders' Rights for this cultivar were applied for in Canada on Dec. 24, 2007 and with the European Union on Jul. 21, 2008. 'Jin Cobule' has not been made publicly available more than one year prior to the filing of this application.

DESCRIPTION OF DRAWING

This new *Lavandula* plant is illustrated by the accompanying photograph which shows blooms, buds, and foliage of the plant in full color. The colors shown are as true as can be reasonably obtained by conventional photographic procedures.

The photograph, taken in Andijk, Netherlands, in mid August 2007 shows 3 about 8 month old plants in a container.

The cultivation of these plants had started in early January in the greenhouse.

DETAILED BOTANICAL DESCRIPTION

The measurements were taken in Hillscheid, Germany, in late October 2008 on 12 month old plants that were growing, 4 plants each, in squared, 32 cm diameter tubs under rain protection at natural temperatures in fall. Culture of these plants had started in the fall of 2007 with planting of rooted cuttings. Flowering season was over at the time of taking plant measurements, yet flower heads were still to be seen. Detailed observations on single flowers had been done already in July.

Color chart used: The Royal Horticultural Society Colour Chart (R.H.S.), 2001.

BRIEF SUMMARY OF INVENTION

The following observations, measurements, and comparisons describe plants grown indoors and outdoors in Andijk, Netherlands, and in Hillscheid, Germany. The following traits have been repeatedly observed and are determined to be basic characteristics of the new variety. The combination of these characteristics distinguishes this *Lavandula* as a new and distinct variety:

1. Blackish blue flower head color with light purple 'wings'
2. Large cone-shaped flower heads
3. Grey green foliage
4. Very well branched and dense, compact plant habit
5. Spreading to mounding, low, plant habit

COMPARISON WITH COMMERCIAL CULTIVARS

'Jin Cobule' differs from the commercial *Lavandula stoechas* cultivar 'Madrid Blue,' synonym 'Bee Happy,' (U.S. Plant Pat. No. 12,573) in that 'Jin Cobule' has a somewhat deeper bluish hue of flower (that is bract) color than 'Bee Happy.' Additionally, 'Jin Cobule' has a more compact and smaller habit than 'Bee Happy.'

'Jin Cobule' differs from the commercial cultivar 'Little Bee Dark Purple' (unpatented) in that 'Jin Cobule' has a slightly more bluish hue of bract color, larger inflorescences, and compact, but not extremely compact plant habit.

Plant:

*Form.*—Perennial, but not hardy in all regions, shrub, stems partly woody.

*Growth and habit.*—Low, very compact bush, dense, freely branched with short internodes, low, spreading to mounding.

*Height.*—33 cm (from top of soil), respective 36 cm height including inflorescences.

*Width (diameter).*—40–50 cm.

*Number of branches.*—About 80–90.

*Number of inflorescences.*—About 70–85.

*Time to produce a finished flowering plant.*—About 4 months for a flowering 12 cm pot.

*Outdoor plant performance.*—Used as patio planters, in container plantings and gardens.

*Time to initiate and develop roots.*—About 10–14 days at 18–21° C.

*Root description.*—Fibrous and freely branching.

*Frost tolerance.*—Up to minus 5° C.

Stem:

*Characteristics.*—Cross section round to square near the tip, side branches are developed at nearly every node.

*Branching characteristics.*—Plants had about 80–90 branches and additional, short secondary branches, secondary branches emerged after flowering season at practically every node.

*Stem length.*—About 28–35 cm.

*Diameter.*—2–3 mm at mid portion.

*Internode length.*—0.7–1.5 cm.

*Color.*—RHS 138A, no anthocyanin.

*Texture.*—Finely pubescent, this is more distinct on the upper parts of the stems Foliage:

*Arrangement.*—Simple leaves, opposite and decussite.

*Leaf shape.*—Linear.

*Apex.*—Acute.

*Base.*—Attenuate to cuneate.

*Margin.*—Entire.

*Leaf length.*—About 2.5–3.5 cm.

*Leaf width.*—About 3 mm.

*Immature leaf, color upper surface.*—Near RHS N138B.

*Immature leaf, color lower surface.*—RHS 138B.

*Mature color upper surface.*—RHS N138C.

*Mature color lower surface.*—Between RHS 189B and 189C.

*Venation type.*—Pinnate to weakly reticulate (difficult because the leaf blade is so narrow).

*Venation color.*—Lower side, mid rib: RHS 193A; venation on upper surface is indistinct.

*Texture.*—Very fine pubescence on upper side, lower side glabrous.

*Fragrance.*—Strong, aromatic.

Inflorescence:

*Blooming habit.*—Natural flowering season was in central Europe is mid summer, flowering period last for about 8–10 weeks.

*Type of inflorescence.*—Flowers in compact verticillasters or spikes, terminal on stems.

*Lastingness of inflorescence.*—Approximately 21 days.

*Shape of inflorescence.*—Compact, resembles a short cone, flowers arranged in small bunches, each of which is subtended by a sepal-like leaflet, the majority of flowers are small, the upper flowers develop relatively large showy bracts.

*Number of flowers per inflorescence.*—Up to 110.

*Length of inflorescence.*—4–5 cm.

*Width of inflorescence.*—1.8–2.0 cm.

*Fragrance.*—Yes.

Peduncle:

*Color.*—RHS 194B.

*Length.*—3–4 cm.

*Diameter.*—2 mm.

*Texture.*—Squared, canescent or pubescent.

Flower/floret:

*Corolla type and shape.*—Majority of flowers are small, tubular, formed by 5 fused petals; terminal flowers have additional 2 relatively large, colored bracts, wing-like.

*Corolla diameter.*—0.4–0.5 cm.

*Length of small flowers.*—About 0.8–0.9 cm.

*Length of terminal flowers.*—Up to 2.8 cm.

*Color of small flowers.*—N92C, or nearly black, N186B.

*Color of terminal flowers, both surfaces.*—Lavender, N81C.

Inflorescence bud:

*Shape.*—Ovate to cone-shaped.

*Diameter.*—2.5–3.0 cm.

*Length.*—1.2–1.3 cm.

*Color (at tight bud).*—Greenish, RHS 138B.

Involucre:

*Shape.*—Each little bunch of flowers is subtended by a cordate involucral bract, the size of which diminishes toward the tip of the inflorescence.

*Bract color.*—RHS 138A, outer surface.

*Length.*—0.6–0.8 cm.

*Width.*—0.8–1.0 cm.

*Apex.*—Obtuse.

*Base.*—Truncate to subcordate.

*Texture.*—Canescent.

Reproductive organs:

Stamens:

*Quantity.*—4.

*Filament, color.*—Whitish, RHS 84D.

*Length.*—4 mm.

*Diameter.*—1 mm.

*Anther color.*—Yellow, RHS 13A.

*Pollen amount.*—Little.

*Pollen color.*—Yellow, RHS 13B.

Pistil:

*Quantity per flower.*—One.

*Length.*—4–5 mm.

*Stigma color.*—Light green, RHS 145C.

*Style color.*—Greenish-white, RHS 157D.

Fruit and seed set: Has not been observed.

Disease and insect resistance: Resistance and susceptibility typical for the species, no special observations made.

What is claimed is:

1. A new and distinct variety of *Lavandula* plant named 'Jin Cobule,' substantially as illustrated and described herein.

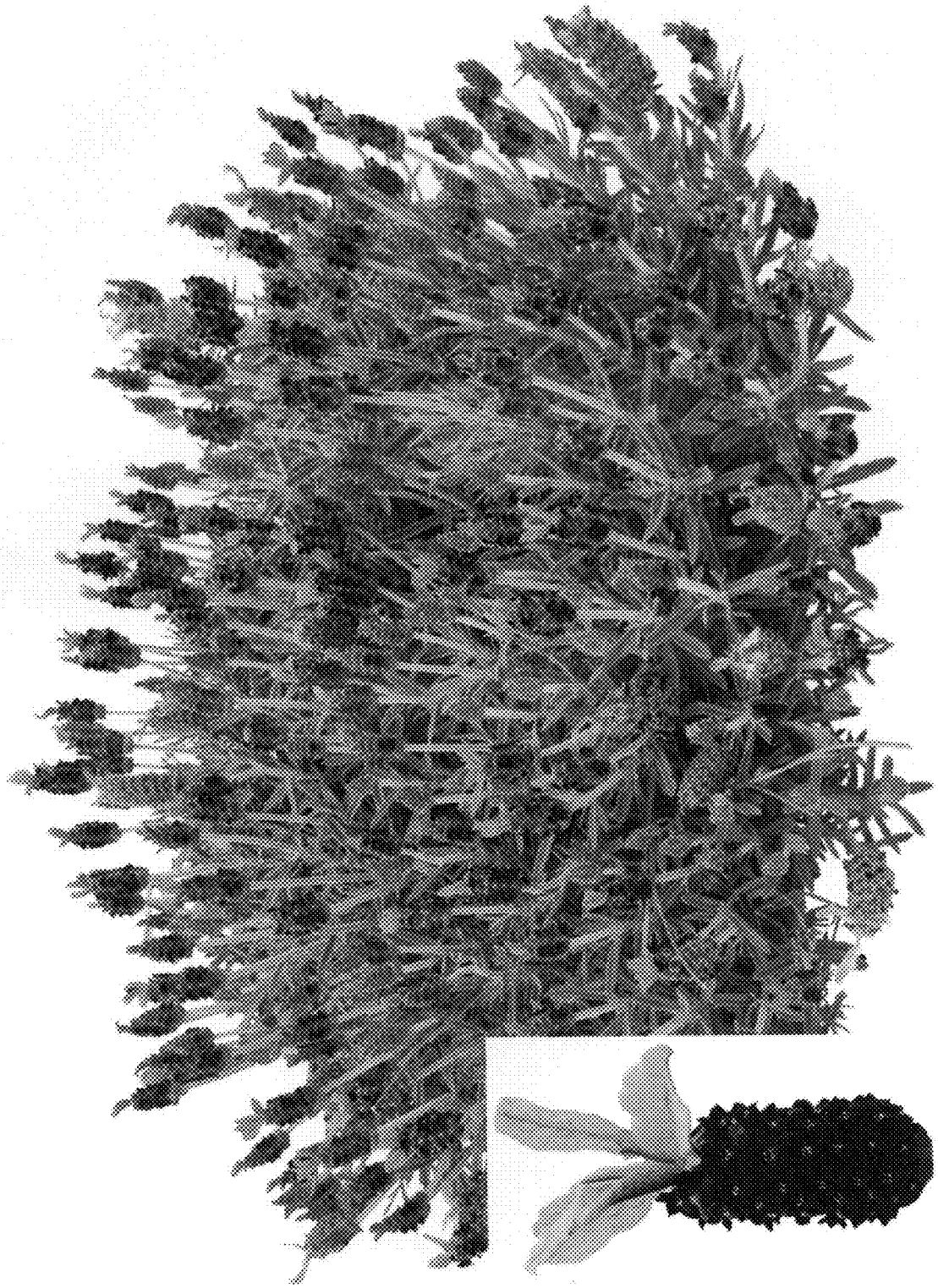

* * * * *